United States Patent [19]

Bamberg et al.

[11] 4,216,328
[45] Aug. 5, 1980

[54] NOVEL INTERMEDIATE FOR PREPARATION OF THERAPEUTICALLY ACTIVE COMPOUNDS

[75] Inventors: Peter Bamberg, Oetwil am See; Ladislas J. S. Végh, Thalwil, both of Switzerland; Emil Hardegger, deceased, late of Gockhausen, Switzerland, by Olga Hardegger, sole heir

[73] Assignee: Astra Lakemedel AB, Sodertalje, Sweden

[21] Appl. No.: 918,724

[22] Filed: Jun. 26, 1978

[30] Foreign Application Priority Data

Jul. 4, 1977 [SE] Sweden .................................. 7707708

[51] Int. Cl.² ............................................ C07D 213/38
[52] U.S. Cl. .................... 546/329; 424/263; 546/302
[58] Field of Search .................... 260/297 R, 296 R; 424/263; 546/329

[56] References Cited

U.S. PATENT DOCUMENTS

| | | | |
|---|---|---|---|
| 3,354,206 | 11/1967 | Wendler et al. | 260/570.8 TC |
| 3,396,224 | 8/1968 | Heyningen | 260/297 R X |
| 3,928,369 | 12/1975 | Berntsson et al. | 260/296 R |
| 3,951,961 | 4/1976 | Ujvari et al. | 542/474 |
| 4,094,908 | 6/1978 | Toth et al. | 260/570 R |

FOREIGN PATENT DOCUMENTS 756893  3/1975  South Africa ........................... 546/329

OTHER PUBLICATIONS

Theilheimer, vol. II, Synthetic Methods of Organic Chemistry, frontis page and p. 210, Interscience Publishers, Inc., N.Y., (1949).
Hoffsommer et al., J. Org. Chem., vol. 28, pp. 1751 to 1753, (1963).
Index Chemicus, vol. 10, No. 6, Abst. 32346, (1963).
Gordon, Psychopharmacological Agents, vol. 1, pp. 54–55, Academic Press, N.Y., (1964).

Primary Examiner—John D. Randolph
Attorney, Agent, or Firm—Brumbaugh, Graves, Donohue & Raymond

[57] ABSTRACT

A novel compound of the formula

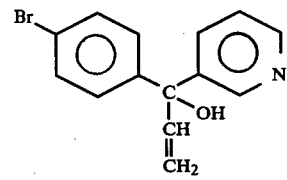

useful in the preparation of therapeutically active compounds, especially compounds useful as antidepressive agents; a process for preparation of said compound and a process for preparing therapeutically active compounds employing said compound as an intermediate.

4 Claims, No Drawings

NOVEL INTERMEDIATE FOR PREPARATION OF THERAPEUTICALLY ACTIVE COMPOUNDS

DESCRIPTION

1. Technical Field

The present invention is related to a new compound, a process for preparation thereof and the use thereof as an intermediate in preparation of therapeutically active compounds.

The object of the invention is to provide an intermediate enabling preparation of therapeutically active compounds with improved economy. A further object of the invention is to provide a process for preparation of therapeutically active compounds via a new reaction route employing a novel intermediate.

2. Background Art

Swedish Pat. No. 361 663 discloses i.a. a compound of the formula

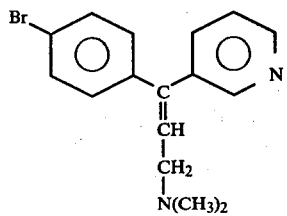

believed to be useful as an anti-depressive agent, and a method for preparation thereof, comprising dehydration of an intermediate of the formula

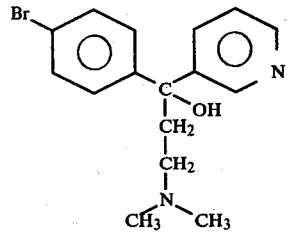

The main disadvantages of the known method is that the preparation of the intermediate is complicated and that only a low overall yield may be obtained.

DISCLOSURE OF INVENTION

The present invention provides a new compound, which may be prepared in a rather simple manner, and which when used as an intermediate in preparation of the therapeutically active compound of formula I above gives improved yield of said compound. The compound of the invention is a compound having the structural formula

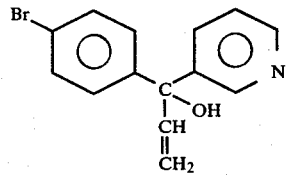

or an acid addition salt thereof.

The compound of the invention may be prepared by reacting a ketone of the formula

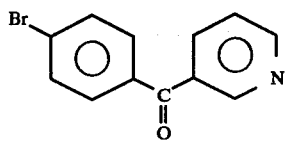

with vinylmagnesiumchloride or vinylmagnesiumbromide. This reaction is suitably carried out by combining a solution of the vinylmagnesiumhalide with the ketone either with cooling or at ambient temperature.

Preparation of the therapeutically active compound may be carried out in the following manner.

The compound of the invention is reacted with one of the following reagents; aqueous hydrochloric acid, aqueous hydrobromic acid, phosphorus trichloride, thionylchloride, phosphorus pentachloride or another halogenating agent or methylsulfonic or toluenesulfonic acid to produce a compound of the formula

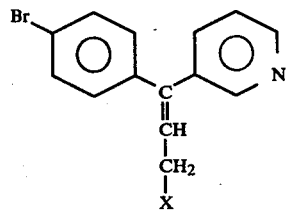

wherein X is a leaving group selected from the halogens such as Br or Cl or methylsulfonyl or toluenesulfonyl. This reaction may be carried out by combining a solution of the compound III with one of the above mentioned halogenating agents which may or may not be dissolved in an organic solvent. The compound thus obtained may then be reacted with dimethylamine to the formation of the end compound. A related therapeutically active compound having the formula

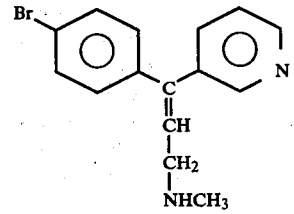

may be obtained by substituting monomethylamine for the dimethylamine in the last reaction step.

The reaction may be carried out with or without external cooling.

The new reaction route for preparing a therapeutically active compound according to the scheme below constitutes a further aspect of the invention.

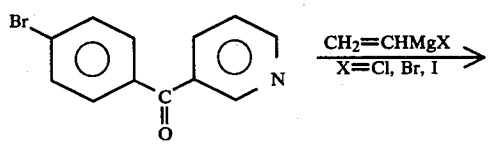

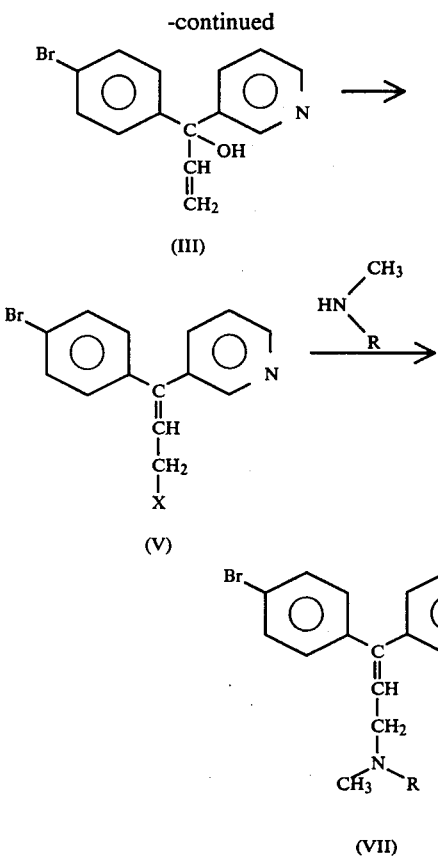

(III)

(V)

(VII)

wherein R is methyl or hydrogen, and X is as defined above.

This reaction sequence may be carried out in a solution without isolation of the intermediate III and V, or preferably with isolation of the intermediate III only.

BEST MODE OF CARRYING OUT THE INVENTION

In a preferred manner the compound III dissolved in 1,2-dichlorethane is added to a suspension of phosphorus pentachloride in the same solvent at 0°–5° C.

The therapeutically active end compound I as well as the related compound VI exist in two stereoisomeric forms, a Z-form and an E-form according to the IUPAC nomenclature. The preferred isomer of each compound is the Z-isomer, having, for compound I, the configuration

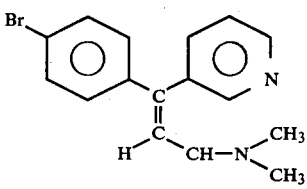

The preferred isomer may be obtained by isolation from an isomeric mixture of the end compound I or by isolation of the corresponding Z-isomer of the intermediate III and using the isomeric pure intermediate in the last reaction step.

The invention is further illustrated by the following examples.

EXAMPLE 1

Step 1. Preparation of vinylmagnesiumchloride

To 24.3 g (1.0 mole) of magnesium covered with 40 ml of dry tetrahydrofuran (THF) were added 20 ml of a vinylchloride solution, obtained by dissolving 66.5 g (1.08 moles) of vinylchloride in 200 ml of THF, and 2–3 iodine crystals, and the temperature was risen to ca 50° C. A Grignard formation started. The remaining vinylchloride solution was added in 10–20 ml portions and the addition was completed in ca 2.5 hours. The reaction was completed by stirring the mixture at 55° C. bath temperature for 1 hour. Then the excess vinylchloride was allowed to evaporate. The brown vinylmagnesiumchloride solution obtained was stored in a refrigerator.

Step 2. Preparation of 3-(4-bromophenyl)-3-(3-pyridyl)-3-hydroxy-prop-(1)-ene 26.2 g (0.1 moles) of 4-bromophenyl-3-pyridylketone were dissolved in 160 ml THF at ca 35° C. This solution was dropped onto ca 45 ml of the vinylmagnesiumchloride/THF solution (step 1, ca 0.13 moles) at ca 0°–5° C. under a gentle argon stream. This procedure took ca 0.5 hrs, provided the bath temperature was ca −5° C. This solution was stirred for further 0.75 hrs after completed addition. 20 ml 20% of aqueous ammonium chloride solution were added under cooling at 0°–5° C. and the suspension was filtered. The filter was washed with 5×25 ml of methylene chloride and the filtrate was evaporated to dryness. The residue was dissolved in 100 ml toluene and evaporated again. The residue, which consisted of the desired tertiary alcohol was thereafter dissolved in 100 ml of 1,2-dichloroethane to the formation of a dark brown solution.

Step 3. Preparation of 3-(4-bromophenyl)-3-(3-pyridyl)-allylchloride

The tert. alcohol solution obtained in step 2 was dropped onto 26 g (0.125 moles) of phosphorpentachloride, which were suspended in 25 ml of 1,2-dichloroethane. This was made at ca 0°–5° C. during ca 30 min. at a bath temperature of −5° to −10° C. This solution was stirred for further 45 min. after completed addition at the same bath temperature. 60 ml of water were dropped in at ca 0°–5° C. during ca 20 min. under stirring. The stirring was stopped and the upper aqueous layer was separated. 60 ml of water were added again and the aqueous layer was separated again. 30 ml of water were added and 15 ml of 25% ammonia soluton were dropped in at ca 0°–5° C. under stirring. The upper layer was separated again. 30 ml of water were added again and 25 ml of 25% ammonia solution were dropped under vigorous stirring at ca 0°–5° C. The upper layer was well separated. The aqueous layers were washed with 30 ml of methylene chloride, which was readded to the reaction solution.

Step 4. Preparation of N,N-dimethyl-3-(4-bromophenyl)-3-(3-pyridyl)-allylamine The brown solution of the chloride from step 3 (from 0.1 moles ketone) in ca 160 ml of solvent was stirred at ca 0° C. and 26 g dimethylamine were added in one portion. This solution was stirred at 0°–5° C. for 2 hours. The solvent was then evaporated. A crude brown oil of the desired end product was obtained.

EXAMPLE 2

The crude brown oil obtained according to example 1 was dissolved in 100 ml of n-butanol. 100 ml water and 20 g (0.2 moles) conc. HCl were added under stirring at 0°–5° C. 15 g of charcoal were added under stirring, the mixture was filtered and the filter was washed with 30 and 20 ml of water. The water phase was separated and washed with 40 ml of n-butanol, this butanol was washed with 40 ml of water. The combined water layers were filtered over 4 g charcoal, the filter was washed with 40 ml of water. The pale yellow water solution obtained (ca 250 ml) was evaporated to dryness, the water was eliminated with further ethanol-toluene distillation. The remaining oil was dissolved in 125 ml technical isopropanol and heated under stirring. The oil dissolved readily and crystallized. This suspension was refluxed for 1.5 hrs, until it was dissolved. Upon cooling Z-N,N-dimethyl-3-(4-bromophenyl)-3-(3-pyridyl)-allylamine hydrochloride cyrstallized readily, the crystalline mass was allowed to stand at room temperature for 2 hours and in the refrigerator (6° C.) for 1 hour. The crystalline mass was filtered, the filter was washed with 3×30 ml cold isopropanol. The filter was dried overnight at room temperature/100 Torr, 23.7 g, further dried at 80° C./100 Torr, for 8 hours, 19.6 g of colourless powder was obtained. M.p.: 186°–194° C. The filtrate was evaporated (not dried). The NMR suggested a content therein of the Z and the E form of N,N-dimethyl-3-(4-bromophenyl)-3-(3-pyridyl)-allylamine hydrochloride in a ratio of about 1 to 2.

Purification:

2.0 g of the crystallized Z-N,N-dimethyl-3-(4-bromophenyl)-3-(3-pyridyl)-allylamine hydrochloride were added to 10 ml 98% isopropanol. The suspension could not be dissolved on refluxing. Further addition of isopropanol, further refluxing did not dissolve the compound. Filtration and drying afforded 1.92 g of Z-N,N-dimethyl-3-(4-bromophenyl)-3-(3-pyridyl)-allylamine hydrochloride.

EXAMPLE 3

To illustrate another way of working up the end compound the filtrate and 15.3 g of the end compound obtained according to example 2 and further 4.3 g of Z-N-N-dimethyl-3-(4-bromophenyl)-3-(3-pyridyl)-allylamine hydrochloride replacing an equal amount obtained according to example 2 were combined and dissolved in water, brought to pH 9–10 with sodiumhydroxide solution and extracted with methylene chloride (slight emulsion). The methylene chloride was dried and evaporated. The dried residue (ca 23 g of an oil) was dissolved in 75 ml of technical isopropanol and heated up to quasi reflux temperature. 50 ml of isopropanol containing 5.4 g of hydrochloric acid (gas) (HCl was introduced in cold isopropanol) were dropped into the solution. After addition of ca ⅔ or ¾ of the isopropanol/HCl, a crystalline mass formed and stirring became difficult. This mass was allowed to stand at room temperature for 2 hours, then at −10° C. for 1 hour. The crystalline mass was filtered and the filter was washed with 4×30 ml of cold isopropanol. The filter was dried at room temperature/100 Torr overnight, then for 8 hours at 80°/100 Torr. 20.9 g of Z-N,N-dimethyl-3-(4-bromophenyl)-3-(3-pyridyl)-allylamine hydrochloride were obtained, m.p. 188°–196° C., as a colourless powder. The filtrate was evaporated and dried overnight at 80° C./100 Torr. 5.8 g, dark yellow powder, close to oily, were obtained. It contained according to NMR the Z-form and the E-form of N,N-dimethyl-3-(4-bromophenyl)-3-(3-pyridyl)-allylamine hydrochloride in a ratio of ca 1 to 6.

Purification:

6.0 g of the crystallized Z-N,N-dimethyl-3-(4-bromophenyl)-3-(3-pyridyl)-allylamine hydrochloride were added to 30 ml 98% isopropanol. The compound was not dissolved but remained as a crystalline mass at reflux temperature. This was allowed to stand at room temperature, then in the refrigerator. Filtration and drying afforded 5.81 g of Z-N,N-dimethyl-3-(4-bromophenyl)-3-(3-pyridyl)-allylamine hydrochloride.

EXAMPLE 4

Step 1. Preparation of 3-(4-bromophenyl)-3-(3-pyridyl)-3-hydroxyprop-(1)-ene

Magnesium 1.281 g (0.0525 mole) in tetrahydrofuran (10 ml) was stirred and kept under a gentle stream of dry argon or nitrogen. To this 3–5 drops of a solution of vinylbromide (5.35 g, 0.05 mole) in 15 ml of tetrahydroduran (THF) were added. The reaction was started with a crystal of iodine and gentle heating. Then, the temperature of the mixture was kept at 45°–50° C. by the addition of vinylbromide solution. The reaction was completed by heating to 60°–70° C. after all vinylbromide has been added. To this solution of vinylmagnesiumbromide was added 4-bromophenyl-3-pyridylketone (10.1 g, 0.0385 mole) in 65 ml of the THF at bout 15° C. After 45 min. at ambient temperature 10 ml of a 20% aqueous ammonium chloride solution were added and the whole mixture was filtered. The filtrate was evaporated yielding a yellow oil which was used directly for the next step. A sample of this oil was crystallized from ether-hexane yielding the pure product, m.p. 68°–70° C.

Step 2. Preparation of 3-(4-bromophenyl)-3-(3-pyridyl)-allylchloride

To a suspension of phosphorus pentachloride (16.2 g, 0.078 mole) in 1,2-dichloroethane (18 ml) the allylic alcohol (17.4 g, 0.05 mole, 85% pure) in the same solvent (60 ml) was added with stirring at 0°–5° C. in an inert gas athmosphere during 20 minutes. The reaction was kept for another 70 min. at about 0° C. Then water (15 ml) was added keeping the temperature below 7° C. The water layer was removed and another 15 ml quantity was added and removed. Then water (15 ml) was added followed by concentrated ammonia until the mixture reacted slightly basic. The aqueous phase was removed and once more water and ammonia were added and removed. All aqueous phases were combined, made basic with ammonia and extracted once with a small amount of methylene chloride. The organic layers were combined, washed once with a small amount of water, dried and stripped, bath temperature 35° C. The dark brown residue was taken up in isopropanol (60 ml) and a slight precipitate formed which consisted of impurities. The mixture was charcoaled and evaporated to 27 ml of total volume. The dark solution was cooled in an ice bath and hydrogen chloride was introduced with stirring until the mixture was acidic. The solution as stirred at room temperature. After scratching the product started to crystallize. After 2 hours at room temperature, 12 hours in a refrigerator and 2 hours in a deepfreezer (−15° C.) the product was collected by filtration. Yield 10.5 g (59.4%) m.p. 156°–159° C. Recrystallization in isopropanyl furnished material with a m.p. 162°–164° C. This product was aminated with dimethylamine according to the procedure given in example 1, step 4. The raw product obtained was analyzed in GLC and consisted of 95.5% Z and 3.5% E-isomer.

Industrial Applicability

The compound and the methods of the invention are useful in the pharmaceutical industry, especially in preparation of a compound of formula VII above in a technical scale.

We claim:

1. An improved process for preparation of a therapeutically active compound of the formula

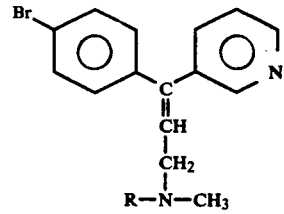

(VII)

wherein R is methyl or hydrogen, or geometrical isomer thereof or a therapeutically acceptable salt of said compound or geometrical isomer in any degree of hydration, staring with the reaction:

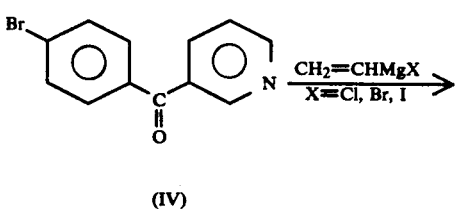

(IV)

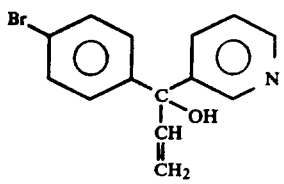

(III)

the improvement comprising

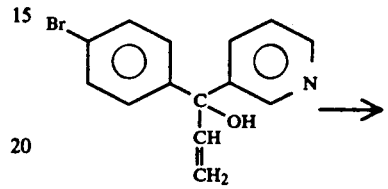

(III)

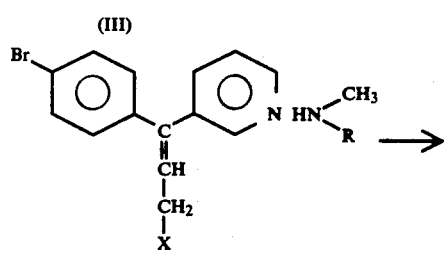

(V)

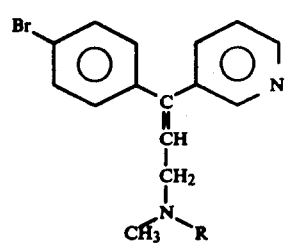

(VII)

wherein X is a leaving group and wherein R is as defined above.

2. A process according to claim 1 characterized in being carried out in a solution without isolation of the intermediate V thereof.

3. The process according to claim 1 characterized in dissolving the compound III in 1,2-dichloroethane and adding the solution to a suspension of phosphorus pentachloride in 1,2-dichlorethane at a temperature of 0°–5° C.

4. A process according to claim 1, wherein the compound III is reacted with a halogenating agent, methylsulfonic acid, or toluenesulfonic acid to effect an allylic rearrangement reaction to the formation of the compound V.

* * * * *

UNITED STATES PATENT AND TRADEMARK OFFICE
CERTIFICATE OF CORRECTION

PATENT NO. : 4,216,328
DATED : Aug. 5, 1980
INVENTOR(S) : Bamberg et al.

It is certified that error appears in the above—identified patent and that said Letters Patent is hereby corrected as shown below:

On the title page, item (75), change "sole heir" to --Ivar C. E. Hardegger-Ullmann, and Beat D. Hardegger-Bächtold, joint heirs--.

<u>Col. 7</u>, <u>line 45</u>, "or" (second occurrence) should read --a--;
<u>line 51</u>, "staring" should read --starting--.

<u>Col. 8</u>, <u>line 52</u>, "The process" should read --A process--.

Signed and Sealed this

Seventh Day of September, 1993

*Attest:*

BRUCE LEHMAN

*Attesting Officer*     *Commissioner of Patents and Trademarks*